United States Patent [19]

Kruse et al.

[11] Patent Number: 4,966,987
[45] Date of Patent: Oct. 30, 1990

[54] FLUORO-CONTAINING 1-ARYLALKOXYTRIS(DIALKYLAMINO)-PHOSPHONIUM SALT, A PROCESS FOR THEIR PREPARATION AND THEIR USE

[75] Inventors: Alfred Kruse, Kelkheim; Günter Siegemund, Hofheim am Taunus; Axel Schumann, Alfter; Ingo W. Ruppert, deceased, late of Bonn, all of Fed. Rep. of Germany, by Carl H. Schroeder, legal representative

[73] Assignee: Hoechst Aktiengesellschaft, Frankfurt am Main, Fed. Rep. of Germany

[21] Appl. No.: 297,424

[22] Filed: Jan. 17, 1989

[30] Foreign Application Priority Data

Jan. 18, 1988 [DE] Fed. Rep. of Germany ....... 3801248

[51] Int. Cl.$^5$ ............................................... C07F 9/02
[52] U.S. Cl. .................................... 558/115; 558/185; 558/199
[58] Field of Search ................. 558/187, 115, 185, 199

[56] References Cited

PUBLICATIONS

P. Simon et al., Synthesis, 1979, 951–952.
Kruse et al., Chem Abst 112-77537u (1990).
P. G. Gassman et al., Tetrahedron Letts. 43, 5243–5246 (1985), esp. 5245, fin. 4.
Chem. Abs., 84:17337X, vol. 84, 1986, p. 471.
Chem. Abs., 84:16935D, vol. 84, 1976, p. 427.
Chem Abs., 93:204151e, vol. 93, 1980, p. 642.

Primary Examiner—Cecilia Shen

[57] ABSTRACT

1-Arylalkoxy-tris(dialkylamino)phosphonium salts of the formula I

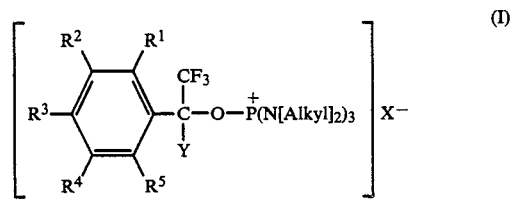

wherein the substituents $R^1$ to $R^5$ are equal or different and represent hydrogen, alkyl having from 1 to 6 carbon atoms which may be perfluorinated, halogen, alkoxy or alkylthio, each having from 1 to 6 carbon atoms, Y represents hydrogen or a perfluoroalkyl group $C_nF_{2n+1}$ having from 1 to 6 carbon atoms, X represents bromine or iodine and "Alkyl" represents an alkyl group of 1 to 3 carbon atoms, at most 3, preferably at most 2, of the groups $R^1$ to $R^5$ having a meaning other than hydrogen and the alkyl, alkoxy and alkylthio substituents attached to the aromatic nucleus altogether containing preferably at most 6 carbon atoms, in particular at most 4 carbon atoms.

The invention also relates to a process for the preparation of the afore-mentioned phosphonium salts and to the use of the compounds of the formula I for the preparation of aromatic compounds having partly fluorinated groups of the formula V

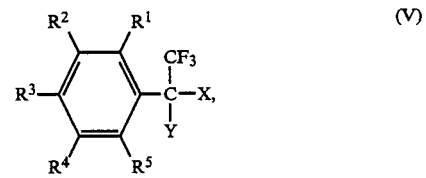

in which $R^1$ to $R^5$, X and Y have the afore-mentioned meaning, X can however also be hydrogen.

14 Claims, No Drawings

FLUORO-CONTAINING 1-ARYLALKOXYTRIS(DIALKYLAMINO)PHOSPHONIUM SALT, A PROCESS FOR THEIR PREPARATION AND THEIR USE

DESCRIPTION

The invention relates to 1-arylalkoxytris(dialkylamino)phosphonium salt of the formula I

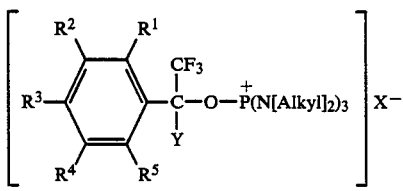

and also to a process for their preparation and their further reaction to give aromatic compounds having a partially fluorinated side chain.

The starting materials used are aromatic aldehydes or ketones which are converted into phosphonium salts of the above formula I by reaction with trifluoromethyl halides and phosphorous triamides.

It is known to prepare alkoxytris(dialkylamino)phosphonium salts by reaction of the corresponding alcohols with a reactive halotris(dialkylamino)phosphonium salt (Synthesis, 1979, 951-2).

The preparation of trifluormethyl-substituted carbinols, the alcohols on which the phosphonium salts of the formula I are based, by transfer of the trifluoromethyl radical to carbonyl compounds is of great interest and has been investigated in many publications. In this process, organometallic compounds of base metals, which are usually prepared from the corresponding trifluoromethyl halide and a metal, such as magnesium, zinc, manganese, etc., are used. The disadvantage of this process is the usually expensive preparation and lability of the organometallic compounds which must be prepared initially, which manifests itself in the poor reproducibility of the published results (Tetrahedron Lett. 26, 5243 to 5246; specifically p. 5245 footnote 4).

The invention accordingly relates to compounds of the formula I (see above) in which the radicals $R^1$ to $R^5$ are identical or different and denote hydrogen, alkyl having 1 to 6 carbon atoms, which can be perfluorinated, alkoxy or alkylthio each having 1 to 6, in particular 1 to 3, carbon atoms, and also halogen (fluorine, chlorine, bromine, iodine), in which, however, not more than three of the radicals $R^1$ to $R^5$ have a meaning other than hydrogen, Y denotes hydrogen or a perfluoroalkyl radical $C_nF_{2n+1}$ having 1 to 6 carbon atoms, X is bromine or iodine and, "alkyl" stands for an alkyl radical having 1 to 3 carbon atoms.

Preferably, no more than two substituents $R^1$ to $R^5$ having a meaning other than hydrogen are bound to the aromatic ring. The alkyl, alkoxy and alkylthio substituents can be straight-chain or branched and advantageously contain overall a maximum of 6, in particular a maximum of 4, carbon atoms.

The invention also relates to a simple one-step process for the preparation of the above-mentioned compounds. This can be achieved by transfer of a trifluoromethyl group to aromatic carbonyl compounds, whereby the preparation and use of the above-mentioned organometallic compounds is avoided, and consists in reacting carbonyl compounds of the general formula II

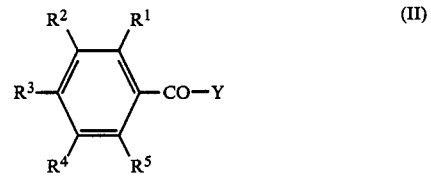

with trifluoromethyl halides of the formula $CF_3X$ (III), in which X is bromine or iodine, and phosphorous tris(dialkylamides) (in other words tris(dialkylamino)phosphanes) of the general formula $P(N[alkyl]_2)_3$ (IV) to give phosphonium salts of the formula I (see above), where in formulae I to III the radicals are $R^1$ to $R^5$, Y and "alkyl" have the above-mentioned meaning. These phosphonium salts are very useful intermediates for syntheses and can be converted - as will be shown later - to aromatics having partially fluorinated side chains, which otherwise are often only accessible with difficulty by other routes.

The process according to the invention does not only have the advantage of being simple, but also the advantage that the starting materials are readily accessible and that without exception good yields of phosphonium salts are obtained. Trifluoromethyl bromide which is less poisonous and cheaper than trifluoromethyl iodide can be used advantageously for the transfer of the trifluoromethyl radical to the carbonyl compounds.

The aromatic carbonyl compounds (II) used can be the aldehydes (Y=hydrogen) or aryl perfluoroalkyl ketones (Y=perfluoroalkyl radical $C_nF_{2n+1}$ where n is 1 to 6). The aromatic carbonyl compounds can be unsubstituted or can have one or more identical or different substituents $R^1$ to $R^5$ having a meaning other than hydrogen. Examples of suitable phosphorous tris(dialkyl) amides (IV) are tris(dimethylamino)phosphane, tris(diethylamino)phosphase and tris(dipropyl- or -isopropylamino)phosphane; preferably, tris(diethylamino)phosphane $P(N[CH_2CH_3]_2)_3$ is used. This phosphane can be produced very easily in high yields by reaction of phosphorus trichloride with diethylamine in a solvent which in inert towards the reactants, for example an aliphatic, cycloaliphatic or aromatic hydrocarbon or a mixture of hydrocarbons. The dialkylamino groups can contain identical or different alkyl groups.

In the reaction of the aromatic aldehydes or ketones (II) with a trifluoromethyl halide (III) and phosphorous tris(dialkyl) amide (IV), initially an adduct of the formula (VI) is formed

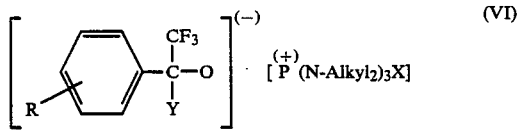

The existence of this compound and the assignment of structure VI becomes plausible from the reactivity observed. This compound differs from compounds I by its reactivity with carboxylic acid halide with the formation of esters and also by the fact that it is converted to the free alcohol by the addition of a proton acid. Compounds I according to the invention do not undergo these reactions. The initially formed adducts VI are subject in the reaction mixture to an exothermic rearrangement to the arylalkoxytris(dialkylamino)phosphonium salts (I) above a conversion temperature which, depending on the type of the underlying alcohol, is between −60° C. and +20° C.

The reaction of the carbonyl compounds with the trifluoromethyl halide and phosphorous tris(dialkyl)amide is in general carried out at temperatures of about −100° C. to +50° C., in particular of −80° to +20° C. In the case of carbonyl compounds of very low reactivity it is advantageous to work at temperatures above −40° C. and, for example, up to +50° C. to achieve a rapid conversion. As is known, the reaction time is dependent on the other conditions, in particular on the reaction temperature. In general, the reaction is completed within a period of a few minutes to several hours.

The reaction is in general carried out without applying superatmospheric pressure. However, it may be advantageous to work at elevated pressure, especially if the reaction is carried out above the boiling temperature (at atmospheric pressure) of the trifluoromethyl halide. This means that in practice the reaction is carried out at least at the internal pressure.

Advantageously, the present process is carried out under anhydrous conditions in the presence of a solvent or diluent which is inert towards the reactants. In particular aprotic liquids are used as liquids of this type. The liquids used are, for example, halogenated hydrocarbons, such as methylene chloride, tetrachloroethane, nitriles, for example acetonitrile or homologues thereof, such as butyronitrile or benzonitrile, esters, such as diethyl carbonate or ethylene carbonate, and ethers, such as tetrahydrofuran or dimethoxyethane. The solvent should, if possible, be anhydrous.

It is advantageous to ensure that during the entire duration of the reaction it is well mixed, for example by stirring, and to keep the reaction product in solution by choosing a suitable solvent.

The method and sequence of combining the three components is not critical. The process according to the invention can be carried out, for example, in such a manner that the solvent, the carbonyl compound and a further component are initially introduced and the third component is metered in. However, it is also possible to combine all three components simultaneously. The other reactants are usually used in at least an equivalent amount with respect to the carbonyl compound II, but often they are used in an excess of, for example, up to 25%.

The reaction mixture can be worked up, for example, by freeing it from the solvent under reduced pressure and recrystallizing the resulting residue. When isolating the phosphonium salt, it may be advantageous first to remove biproducts and some of the solvent by extraction of the reaction mixture with a non-porous solvent, for example a hydrocarbon such as hexane. In this operation, the bottom layer, which contains mostly the phosphonium salt I, is often already present as a solid.

The phosphonium salts according to the invention are fairly stable, hydrolysis-resistant solids, which are readily soluble in water and polar solvent. Furthermore, they are preparatively very useful compounds, which can be easily converted in one step to other interesting aromatic compounds having partially fluorinated side chains. Thus, when the phosphonium salts I are heated, cleavage of the carbon-oxygen bond at the carbonyl carbon atom takes place, and a molecule of phosphoric triamide P(0) (N[alkyl]₂)₃ is eliminated with substitution by the halide ion. In this reaction, aromatic compounds of the general formula V

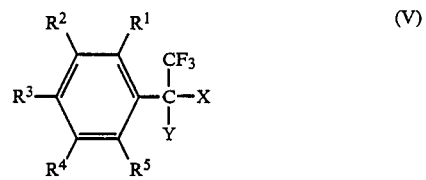

which are known per se and contain bromine or iodine at the α-position of the fluorinated side chain and in which $R^1$ to $R^5$ and Y have the above-mentioned meanings are formed. In most cases, this cleavage proceeds almost quantitatively. For this purpose, the phosphonium salt is heated undiluted or in an inert solvent, for example one having a boiling point of at least the melting temperature of the phosphonium salt, such as methyl isobutyl ketone, tetrahydronapthalene, usually to temperatures above melting point. If a solvent is used, the conversion takes place even at temperatures below the melting point. In the case of individual phosphonium salts, for example the product from Example 5, it is also possible to use fairly low-boiling solvents, such as acetone. The reaction conditions are not critical; the two reaction products are easily separated by distillation.

In a further step, the halides V thus obtained can be easily reduced to the corresponding α-hydrogen perfluoroalkyl aromatics of the formula V in which X denotes hydrogen. The reduction can be carried out by reaction with hydrogen on noble metal catalysts, such as platinum on activated carbon, or more simply by thermal reaction of the halide V with an organic, hydrogen-releasing compound, such as reactive alkyl aromatics, such as tetrahydronaphthalene or diphenylmethane. For this purpose, the compound to be reduced is heated with the alkyl aromatic to temperatures of usually 160° C. to 220° C. This reduction can also be carried out in one step, starting from the phosphonium salts I, since under these reaction conditions a rapid conversion to the halide V takes place. The reaction product can be isolated, for example by distillation. This reaction sequence provides a convenient access to aromatic compounds of the structure V having fluorinated side chains. These compounds are interesting intermediates, which previously could only be prepared in complicated and multi-step syntheses.

The structures of the compounds according to Examples 1 to 7 and their most important physical data are summarized in the Table. In as far as solvent mixtures were used in the examples for recrystallization, a ratio by volume of 1:1 was used, it being possible, however, to achieve optimizations, even with respect to the yield, by changing the ratio.

EXAMPLES 1–7

Compounds of the formula (I)

(1) In a round-bottom flask, 41 g (0.27 mol) of trifluoromethyl bromide are condensed in the absence of moisture at about −70° C. into a solution of 26.5 g (0.25 mol) of benzaldhyde in 150 ml of $CH_2Cl_2$. Over a period of half an hour, 66.7 g (0.27 mol) of phosphorous tris(diethyl)amide are then metered in with stirring. After 4 hours at −70° C., the aldehyde had been converted according to IR spectroscopy. The reaction mixture was then slowly heated to room temperature, and the solvent evaporated under reduced pressure. Recrystallization of the crude product from methyl t-butyl ether/ethyl acetate gave 97.2 g (77% of yield) of colorless crystals of (1-phenyl-2,2,2-trifluoroethoxy)tris(diethylamino)phosphonium bromide of melting point 129° C.

(2) In a round-bottom flask, 61.7 g (0.25 mol) of phosphorous tris(diethyl)amide are added with stirring and in the absence of moisture at about 0° C. to a solution of 39.6 g (0.25 mol) of 2-chloro-6-fluorobenzaldehyde in 150 ml of butyronitrile. 42.5 g (0.28 mol) of trifluoromethyl bromide are then passed into the solution at 20° to 25° C. at the rate at which it is consumed. After about 4 hours, the conversion was complete. The reaction mixture was extracted twice with 200 ml each of hexane. The extraction residue was freed from residual solvent under reduced pressure. Recrystallization of the residue obtained (123 g) from tetrahydrofuran gave 104 g (75% of yield) of [1-(2-chloro-6-fluorophenyl)-2,2,2-trifluoroethoxy]tris(diethylamino)phosphonium bromide in the form of colorless hygroscopic crystals of melting point 123° to 124° C.

(3) In a round-bottom flask, 41 g (0.27 mol) of trifluoromethyl bromide were condensed in the absence of moisture at about −70° C. into a solution of 34.3 g (0.25 mol) of ω,ω,ω-trifluoroacetophenone in 150 ml of $CH_2Cl_2$. At this temperature, 66.7 g (0.27 mol) of phosphorous tris(diethyl)amide were then added dropwise over a period of one hour and with thorough stirring. After a further 6 hours, the reaction mixture was slowly warmed to room temperature and extracted twice with 200 ml each of hexane. The extraction residue was freed from residual solvent under reduced pressure. Recrystallization of the residue obtained (161 g) from tetrahydrofuran/acetone gave 121 g (85% of yield) of [1-phenyl-2,2,2-trifluoro-1-(trifluoromethyl)ethoxy]tris(diethylamino)phosphonium bromide in the form of colorless crystals of melting point 168° C.

The compounds according to Examples 4 to 7 listed in the Table were prepared by the process according to Example 3.

EXAMPLES 8–11

Compounds of the formula (V)

(8) In a distillation apparatus, 50 g (0.1 mol) of (1-phenyl-2,2,2-trifluoroethoxy)tris(diethylamino)phosphonium bromide (obtained according to Example 1) were melted and heated to 140° C. for a short time. The subsequent distillation gave 23.5 g (99% of yield) of (1-bromo-2,2,2-trifluoroethyl)benzene (b.p. 68° C./15 mbar) and also 24.9 g (95% of yield) of phosphoric tris(diethyl)amide as additional product.

(9) In a round-bottom flask equipped with reflux condenser, 53.2 g (0.1 mol) [1-(4-methoxyphenyl)-2,2,2-trifluoroethoxy]tris(diethylamino)phosphonium bromide (product from Example 5) were refluxed in 80 ml of methyl isobutyl ketone for 10 minutes. The subsequent distillation gave 22.2 g (83% of yield) of 1-(1-bromo-2,2,2-trifluoroethyl)-4-methoxybenzene (b.p. 108° to 110° C./8 mbar).

(10) In distillation apparatus, a mixture of 50 g (0.1 mol) of (1-phenyl-2,2,2-trifluoroethoxy)tris(diethylamino)phosphonium bromide according to Example 1 and 40 g (0.3 mol) of tetrahydronaphthalene were heated for 2 hours at about 200° C. After about an hour, the reaction product was slowly distilled off through a small column, in which the boiling temperature at the column head did not exceed 140° C. The remaining product was distilled off from the reaction mixture at 40 mbar, after the reaction was completed. Repeated distillation of the combined fractions gave 10.2 g (64% of yield) of (2,2,2-trifluoroethyl)benzene of b.p. 71° to 72° C./100 mbar.

(11) In a distillation apparatus, a mixture of 57 g (0.1 mol) of [1-phenyl-2,2,2-trifluoro-1-(trifluoromethyl)ethoxy]tris(dialkylamino)phosphonium bromide according to Example 3 and 40 g (0.3 mol) of tetrahydronaphthalene was heated at 200° C. for 3 hours. After about an hour, the reaction product was slowly distilled off through a column, in which the boiling temperature at the column head did not exceed 160° C. After the reaction was completed, the remaining product was distilled off from the reaction mixture at 20 mbar. Repeated distillation of the combined fractions gave 12.8 g (56% of yield) of 1,1,1,3,3,3-hexafluoro-2-phenylpropane (b.p. 83° to 84° C./100 mbar).

COMPARATIVE EXAMPLE

The fact that in the reaction of the starting products used according to the invention initially a salt-like adduct of the formula VI is formed, which differs from the compounds I according to the invention by its reactivity with carboxylic acid halides with a formation of esters, is confirmed by the following comparative experiment with respect to Example 3:

As in Example 3, the same amounts of ω,ω,ω-trifluoroacetophenone, $CH_2Cl_2$, trifluromethyl bromide and phosphorous tris(diethyl)amide are combined. Four hours after the addition of phosphorous tris(diethyl)amide was complete, 35.1 g (0.25 mol) of benzoyl chloride were added. The mixture was subsequently stirred at −70° C. for 2 hours. After warming the reaction mixture to room temperature, 300 ml of hexane were added. After phase separation, the bottom layer was again carefully extracted with hexane. The combined hexane layers were concentrated and distilled under reduced pressure. This gave 32.5 g (75%) of 1,1,1,3,3,3-hexafluoro-2-phenylpropyl 2-benzoate of boiling point 96° to 97° C./0.1 mbar.

| C | H | F | $^{19}$F-NMR |ppm| |
| --- | --- | --- | --- |
| (calc.) | (calc.) | (calc.) | $CF_3$ |
| found | found | found | |
| (55.18) | (2.89) | (32.74) | −70.5 |
| 55.0 | 2.9 | 32.7 | |

In a different experiment, 11.4 g (0.02 mol) of the phosphonium salt from Example 3 and 2.8 g (0.02 mol) of benzoyl chloride were stirred in a round-bottom flask in 50 ml of $CH_2Cl_2$. Even after two hours of refluxing, the two starting materials were still present side by side without change; the formation of the ester described above was not observed.

TABLE

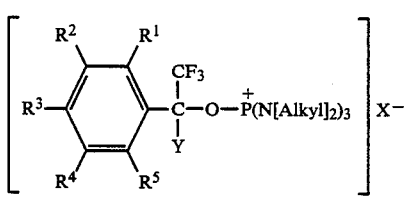

| Ex. | R | Y | m.p. [°C.] (recrystallized from) | C (calc.) found | H (calc.) found | F (calc.) found | $^{19}$F—NMR [ppm] —CF$_3$ (CDCl$_3$) | Yield |
|---|---|---|---|---|---|---|---|---|
| 1 | H | H | 129 (EA/MtBE) | (47.81) 47.7 | (7.22) 7.4 | (11.34) 10.7 | −76.4 | 77% |
| 2 | 2-Cl, 6-F | H | 123-4 (THF) | (43.3) 43 | (6.18) 6.1 | (13.7) 13.6 | −75.4 | 75% |
| 3 | H | CF$_3$ | 168 (THF/Acetone) | (44.22) 43.8 | (5.88) 6.1 | (19.98) 19.9 | −71.2 | 85% |
| 4 | 4-CH$_3$ | H | 148 (THF) | (48.84) 49.2 | (7.42) 7.2 | (11.03) 11.0 | −76 | 71% |
| 5 | 4-OCH$_3$ | H | 117-8 (Acetone) | (47.37) 47.1 | (7.19) 7.1 | (10.7) 10.6 | −76.6 | 81% |
| 6 | 3,4(CH$_3$)$_2$ | CF$_3$ | 118-9 (MiBK) | (46.16) 46.2 | (6.57) 6.5 | (19.05) 18.7 | −71.0 | 84% |
| 7 | H | C$_2$F$_5$ | 137 (MiBK) | (42.59) 43.2 | (5.64) 5.6 | (24.5) 24.4 | −66.1 | 61% |

EA = Ethyl acetate
MtBE = Methyl t.-butyl ether
THF = Tetrahydrofuran
MiBK = Methyl isobutyl ketone

We claim:

1. 1-Arylalkoxy-tris(dialkylamino)phosphonium salts of the formula I

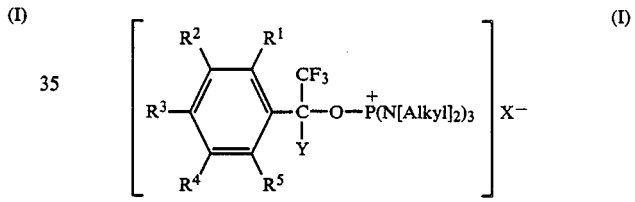

wherein the substituents $R^1$ to $R^5$ are equal or different and represent hydrogen, alkyl having from 1 to 6 carbon atoms which may be perfluorinated, halogen, alkoxy or alkylthio, each having from 1 to 6 carbon atoms, Y represents hydrogen or a perfluoroalkyl group $C_nF_{2n+1}$ having from 1 to 6 carbon atoms, X represents bromine or iodine and "Alkyl" represents an alkyl group of 1 to 3 carbon atoms, at most 3 of the groups $R^1$ to $R^5$ having a meaning other than hydrogen.

2. A compound according to claim 1, wherein at most 2 of the groups $R^1$ to $R^5$ have a meaning other than hydrogen.

3. A compound as claimed in claim 1, wherein the alkyl, alkoxy and alkylthio substituents attached to the aromatic nucleus altogether contain at most 6 carbon atoms.

4. A compound as claimed in claim 2, wherein the alkyl, alkoxy and alkylthio substituents attached to the aromatic nucleus altogether contain at most 6 carbon atoms.

5. A compound as claimed in claim 1, wherein the alkyl, alkoxy and alkylthio substituents attached to the aromatic nucleus altogether contain at most 4 carbon atoms.

6. A compound as claimed in claim 2, wherein the alkyl, alkoxy and alkylthio substituents attached to the aromatic nucleus altogether contain at most 4 carbon atoms.

7. A process for the preparation of 1-aryloxy-tris(-dialkylamino)phosphonium salts of the formula I (I)

wherein the substituents $R^1$ to $R^5$ are equal or different and represent hydrogen, alkyl having from 1 to 6 carbon atoms which may be perfluorinated, halogen, alkoxy or alkylthio each having from 1 to 6 carbon atoms, Y represents hydrogen or a perfluoroalkyl group $C_nF_{2n+1}$ having from 1 to 6 carbon atoms, X represents bromine or iodine and "Alkyl" represents an alkyl group of 1 to 3 carbon atoms, at most 3 of the groups $R^1$ to $R^5$ having a meaning other than hydrogen, which comprises reacting an aromatic carbonyl compound of the formula II

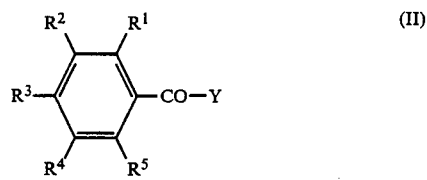

with a trifluoromethyl halide of the formula CF$_3$X (III) and a trisdialkylamide of phosphorous acid of the formula P(N(Alkyl|$_2$)$_3$ (IV), in formulae II, III and IV $R^1$ to $R^5$, Y, X and Alkyl having the afore-mentioned meaning.

8. A process as claimed in claim 7, wherein the reaction is carried out at a temperature in the range of from about −100° C. to +50° C.

9. A process as claimed in claim 8, wherein the reaction is carried out at a temperature in the range of from −80° C. to +20° C.

10. A process as claimed in claim 7, wherein the reaction is carried out at ambient pressure.

11. A process as claimed in claim 7, wherein the reaction is carried out at a pressure higher than ambient pressure and at a temperature which is above the boiling point (at ambient pressure) of the trifluoromethyl halide.

12. A process as claimed in claim 7, which is carried out under anhydrous conditions in the presence of a solvent or diluent inert towards the reactants.

13. A process as claimed in claim 7, wherein in relation to carbonyl compound II, the other reactants are applied in at least a stoechiometric amount and at most an amount exceeding the stoechiometric amount by 25%.

14. 1-Arylalkoxy-tris(dialkylamino)phosphonium salts of the formula I

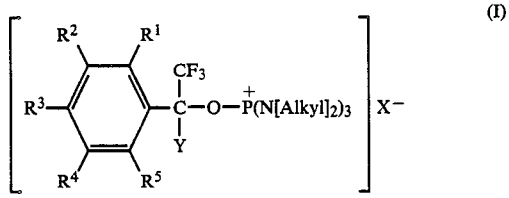

wherein the substitutents $R^1$ to $R^5$ are equal or different and represent hydrogen, alkyl having from 1 to 3 carbon atoms, fluorine, chlorine or bromine, alkoxy having from 1 to 3 carbon atoms, Y represents hydrogen or a perfluoroalkyl group $C_nF_{2n+1}$ having from 1 to 6 carbon atoms, X represents bromine or iodine and "Alkyl" represents an alkyl group of 1 to 3 carbon atoms, at most 3 of the groups $R^1$ to $R^5$ having a meaning other than hydrogen.

* * * * *